(12) United States Patent
Garrison et al.

(10) Patent No.: US 6,520,984 B1
(45) Date of Patent: Feb. 18, 2003

(54) STENT GRAFT ASSEMBLY AND METHOD

(75) Inventors: Michi E. Garrison, Half Moon Bay, CA (US); Leon V. Rudakov, Belmont, CA (US)

(73) Assignee: CardioVasc, Inc., Menlo Park, CA (US)

( * ) Notice: Subject to any disclaimer, the term of this patent is extended or adjusted under 35 U.S.C. 154(b) by 0 days.

(21) Appl. No.: 09/560,427

(22) Filed: Apr. 28, 2000

(51) Int. Cl.$^7$ .................................................. A61F 2/06
(52) U.S. Cl. ..................................................... 623/1.11
(58) Field of Search ............................... 623/1.11, 1.12, 623/1.13, 1.14, 1.15, 1.16, 1.17, 1.18, 1.19, 1.2, 1.21; 606/108, 191, 194, 195, 198

(56) References Cited

U.S. PATENT DOCUMENTS

| | | | |
|---|---|---|---|
| 4,656,083 A | 4/1987 | Hoffman et al. | |
| 5,217,492 A | 6/1993 | Guire et al. | |
| 5,591,140 A | 1/1997 | Narayanan et al. | |
| 5,643,580 A | 7/1997 | Subramaniam | |
| 5,653,747 A | 8/1997 | Dereume | |
| 5,667,523 A | * 9/1997 | Bynon et al. | ................ 606/198 |
| 5,674,241 A | 10/1997 | Bley et al. | |
| 5,697,971 A | 12/1997 | Fischell et al. | |
| 5,776,141 A | * 7/1998 | Klein et al. | ................ 606/108 |
| 5,843,117 A | 12/1998 | Alt et al. | |
| 5,865,723 A | 2/1999 | Jayaraman | |
| 5,866,113 A | 2/1999 | Hendriks et al. | |
| 5,911,754 A | 6/1999 | Kanesaka et al. | |
| 5,980,530 A | * 11/1999 | Willard et al. | ............... 606/108 |
| 5,980,565 A | 11/1999 | Love | |
| 6,010,530 A | 1/2000 | Goicoechea | |
| 6,019,789 A | 2/2000 | Dinh et al. | |
| 6,022,374 A | 2/2000 | Imran | |
| 6,066,167 A | 5/2000 | Lau et al. | |
| 6,106,548 A | 8/2000 | Roubin et al. | |
| 6,350,277 B1 | * 2/2002 | Kocur | ........................ 623/1.11 |

FOREIGN PATENT DOCUMENTS

WO    WO98/46168    4/1998

* cited by examiner

Primary Examiner—Michael J. Milano
Assistant Examiner—Vy Q. Bui
(74) Attorney, Agent, or Firm—Peter J. Dehlinger; Larry W. Thrower; Perkins Coie LLP

(57) ABSTRACT

A stent graft assembly for use in placing a stent graft in a vessel of a patient comprising a balloon delivery catheter having a distal extremity and having an inflatable balloon on the distal extremity. A stent graft disposed over the inflatable balloon. The stent graft comprises a stent and a graft in the form of a polymeric sleeve extending over at least a portion of the graft. The graft has first and second ends. First and second expandable security rings are disposed over the first and second ends of the graft and serve to secure the first and second ends of the graft to the stent to prevent inadvertent displacement of the graft with respect to the stent during deployment of the stent graft into the vessel of the patient.

8 Claims, 1 Drawing Sheet

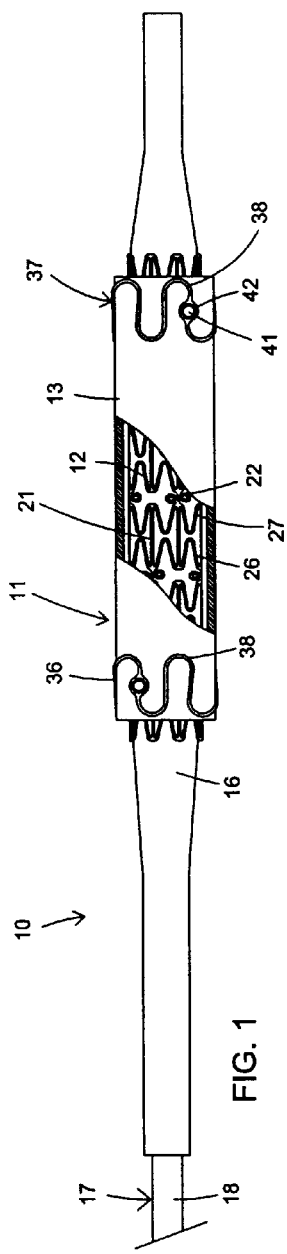
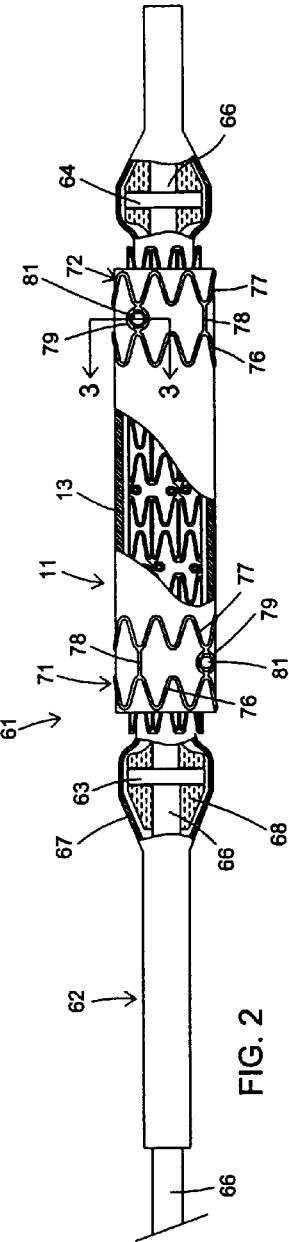
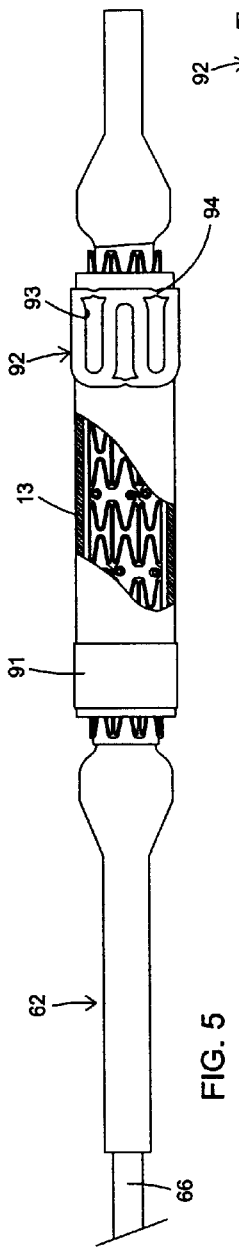
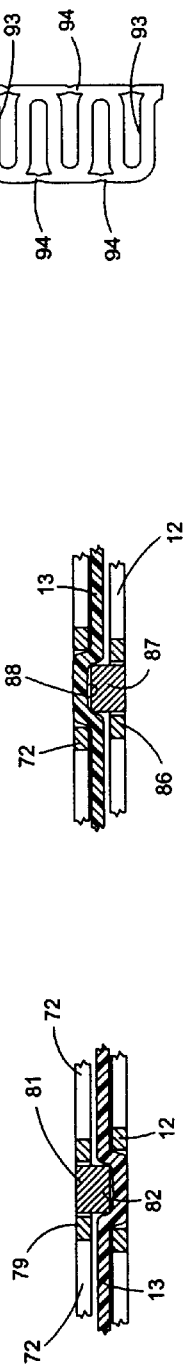

STENT GRAFT ASSEMBLY AND METHOD

This invention relates to a stent graft assembly and method and more particularly to a stent graft assembly which includes security rings.

In co-pending application Ser. No. 09/385,691 filed on Aug. 30, 1999, there is disclosed a composite expandable device with polymeric covering and bioactive coating thereon, delivery apparatus and method. In connection with the expandable stent and the polymeric covering forming a graft carried thereby it has been found that it may be possible for the stent to move or become dislodged from its most desirable position on the stent. There is therefore a need for a new and improved stent graft assembly and method which overcomes this possible difficulty.

In general, it is an object of the present invention to provide a stent graft assembly and method in which security rings form a part of the stent graft assembly.

Another object of the invention is to provide an assembly of the above character in which the security rings are placed on the ends of the graft.

Another object of the invention is to provide an assembly of the above character in which the security rings can readily accommodate expansion of the stent graft.

Another object of the invention is to provide an assembly of the above character in which a radiopaque marker is carried by the security ring.

Another object of the invention is to provide a stent graft assembly of the above character which can be utilized with conventional balloon delivery catheters.

Additional objects and features of the invention will appear from the following description in which the preferred embodiments are set forth in detail in conjunction with the accompanying drawings.

FIG. 1 is a side elevational view of a stent graft assembly incorporating the present invention mounted on the distal extremity of a balloon delivery catheter.

FIG. 2 is a side elevational view of another embodiment of a stent graft assembly incorporating the present invention also mounted on the distal extremity of a balloon delivery catheter.

FIG. 3 is a cross-sectional view taken along the line 3—3 of FIG. 2.

FIG. 4 is a view similar to FIG. 3 showing an alternate embodiment.

FIG. 5 is a side elevational view of a stent graft assembly with a certain portion of the stent graft being removed and showing the use of different types of security rings.

FIG. 6 is an enlarged view of one of the security rings shown in FIG. 5.

In general, the stent graft assembly incorporating the present invention is for use in placing a stent graft in a vessel of a patient and comprises a balloon delivery catheter having a distal extremity and having an inflatable balloon on the distal extremity. A stent graft is disposed over the inflatable balloon and is comprised of a stent and an outer polymeric sleeve, the sleeve having first and second ends. First and second expandable security rings are disposed over the first and second ends of the graft and serve to secure the first and second ends of the graft to the stent to prevent inadvertent displacement of the sleeve with respect to the stent during deployment of the stent graft into the vessel of the patient.

More particularly as shown in FIG. 1 of the drawings, the stent graft assembly 10 includes a stent graft 11 which consists of a stent 12 which is covered by a polymeric sleeve 13. As shown in FIG. 1, the stent graft 11 is disposed over an inflatable balloon 16 on the distal extremity of a balloon delivery catheter 17 of a conventional type and forming a part of the assembly 10. The balloon delivery catheter 17 includes a multi-lumen shaft 18 which incorporates a balloon inflation lumen (not shown) and may incorporate a guide wire lumen (not shown).

The balloon delivery catheter 17 and the stent graft 11 consisting of stent 12 and the polymeric sleeve 13 are disclosed in co-pending application Ser. No. 09/385,691 filed on Aug. 30, 1999, and therefore will not be described in detail. As disclosed therein, the stent 12 is in the form of an expandable frame and consists of a plurality of axially spaced-apart circular belts 21 which are interconnected by sinusoidal interconnector 22. Each belt 21 is comprised of a plurality of circumferentially spaced-apart elongate struts 24. Sinusoidal-shaped elements 26 and 27 adjoin the ends of the struts 24 and form in conjunction therewith the circular belts 21. The sinusoidal-shaped interconnectors 22 provided for interconnecting the belts 21 are at circumferentially spaced-apart positions to provide a stent 12 which when expanded is capable of providing circumferential support while at the same time being axially flexible.

The stent 12 is typically formed of a suitable metal such as stainless steel, titanium and other metals and alloys thereof. It is desirable that the material utilized for the frame be biocompatible with the fluids and tissue of the human body.

The sleeve 13 is in the form of a tubular member of a size so that it can slip over the stent 12 when it is in an unexpanded condition and preferably has a length so that the extreme ends of the stent 12 extend beyond the sleeve as shown in FIG. 1. The sleeve 13 is typically formed of a polymeric material such as ePTFE.

In order to ensure that the polymeric sleeve 13 remains in the desired position on the stent 12, security rings 36 and 37 have been positioned over the outer ends of the sleeve 13. The security rings 36 and 37 typically can be formed of a metal and preferably the same metal which is used for the stent 12 as for example stainless steel or titanium or alloys thereof. The rings 36 and 37 have sinusoidal-shaped convolutions 38 so that they can be expanded with the stent graft when the stent graft is expanded as hereinafter described. By way of example, the security rings can be formed from laser cut tubing in the same manner as stents having a suitable wall thickness of 0.003" to 0.006". The inner surfaces of the security rings can be left unpolished so that they have a rougher inner surface finish to enhance gripping to the outer surface of the sleeve 13. Alternatively, a texture can be applied to the inner surface to enhance the gripping capabilities of the security ring.

A radiopaque marker 41 is carried by at least one and if desired both of the security rings 36 and 37. Thus as shown, a radiopaque marker 41 is provided on the security ring 37 and can be of a suitable radiopaque material such as gold which has been cold worked or forged into an eyelet receptacle 42 formed as a part of the convolutions 38.

In use of the stent graft assembly 10 and the stent graft 11 of the present invention with the method of the present invention, the stent 12 can be placed upon a support mandrel (not shown) after which the sleeve 13 is slipped onto the stent graft to provide the stent graft 11. The stent graft 11 is then placed on the balloon 16 of the balloon delivery catheter 17. The stent graft 11 is then crimped onto the balloon 16 with a crimping tool (not shown). The security rings 36 and 37 are then placed over the sleeve 13 and crimped onto the ends of the sleeve 13 by a crimping tool to ensure that the security rings 36 and 37 remain in place on the ends of the sleeve 13 and also to ensure that the ends of the graft 11 frictionally engage the stent 12 to retain the sleeve 13 in the desired position on the stent 12. Alternatively, the security rings 36 and 37 and the stent graft 11 can be crimped simultaneously.

The stent graft assembly 10 shown in FIG. 1 can now be utilized for positioning the stent graft 11 in a vessel of a patient in a conventional manner as for example by introducing the same through a femoral artery. The advancement of the stent graft 11 can be ascertained by observing the positioning of the radiopaque marker 41 and also by any radiopaque markers on the stent 12 and the balloon catheter 17. During advancement of the stent graft to the desired site, the security rings 36 and 37 serve to ensure that the sleeve 13 will not accidentally become dislodged or shifted in position on the stent 12. After the stent graft has been delivered to the desired position in the vessel of the patient, the balloon 16 of the balloon delivery catheter 17 can be expanded to expand the stent 12 and the sleeve 13 carried thereby as well as the security rings 36 and 37.

After the stent graft 11 has been delivered and then expanded the desired amount, the balloon 16 of the balloon delivery catheter 17 can be deflated and the balloon delivery catheter 17 removed in a conventional manner. The stent graft 11 will remain in place. Its position can be ascertained by observing the position of the radiopaque marker 41.

Another embodiment of a stent graft assembly incorporating the present invention is shown in the stent graft assembly 61 in FIG. 2. The balloon delivery catheter 62 shown therein shows the use of radiopaque marker bands 63 and 64 positioned on a shaft 66 on opposite ends of the balloon 67 and held in place by suitable means such as an epoxy 68 and disposed on opposite ends of the stent graft 11 and serve as enlargements to prevent the inadvertent dislodgement of the stent and/or the graft from the balloon during deployment of the stent graft 11.

In addition as in the previous embodiments, security rings 71 and 72 are provided on opposite ends of the stent 12 and the sleeve 13. Security rings 71 and 72 are each comprised of two elongate elements 76 and 77 in the forms of waves or convolutions which are sinusoidal in shape and which are joined together by circumferentially spaced-apart axially extending struts 78 and eyelets 79. As with the security rings 36 and 37, it can be seen that the security rings 71 and 72 can be readily crimped into place and expanded in the same manner as the security rings 36 and 37. The eyelets 79 carry radiopaque markers 81. As with the security rings 36 and 37 the inner surfaces of the elements 76 and 77 can be left unpolished or with a textured surface for frictionally engaging the outer surface of the polymeric sleeve 13.

In order to further enhance the engagement between the polymeric sleeve 13 on the stent 12, the radiopaque marker 81 as shown in FIG. 3 can protrude out of the eyelet 79 so that it can form an indentation 82 with the sleeve 13 which extends into an open space in the stent 12 to further ensure a good engagement between the sleeve 13 and the stent 12 to prevent dislodgement of the sleeve 13 and ring 71 or 72 from the stent 12. In a similar manner as shown in FIG. 4, an eyelet 86 provided on the stent 12 may also carry a radiopaque marker 87 protruding radially and forming an indentation 88 in the inner surface of the sleeve 13 and to extend into a space in the security ring 72 to further ensure good engagement between the sleeve 13 and the stent 12.

Operation and use of the stent graft assembly 61 shown in FIG. 2 is very similar to that hereinbefore described with respect to FIG. 1 with the principal difference being that the security rings 71 and 72 have enhanced friction engaging capabilities over the security rings 36 and 37 shown in FIG. 1. In addition, the balloon delivery catheter 62 by providing the marker bands 63 and 64 on opposite extremities of the stent graft 11 also ensure that the stent graft 11 cannot accidentally become dislodged during deployment of the stent graft 11.

Still another embodiment of a stent graft assembly incorporating the present invention is shown in FIG. 5 in which the balloon delivery catheter 62 as shown therein is similar to the one hereinbefore described. The stent graft 11 is also similar to those hereinbefore described. However, in FIG. 5 there is shown the use of security rings 91 or 92 (showing two different designs) mounted on opposite ends of the sleeve 13. The security ring 91 is in the form of a stretchable polymer which can be stretched and fitted over one end of the sleeve 13 to frictionally retain the security ring 91 on the sleeve 13 and similarly to retain the sleeve 13 on the stent 12. Alternatively as shown with the security ring 92, a less stretchable band of polymeric material can be utilized which is provided with circumferentially spaced-apart cutouts 93 therein which as shown in detail in FIG. 6 are positioned in such a manner so as to provide weakened regions 94 associated with each of the cutouts 93 but being staggered or provided on opposite sides of the security ring 92 so that when the stent graft 11 is expanded, these weakened regions will or can break apart to provide a zig-zag shape or a substantially sinusoidal wave-like shape for the expanded security ring 92. Thus it can be seen that a polymeric security ring can be provided which firmly secures the graft to the stent while still permitting expansion of the stent and graft after the stent graft assembly 11 has been deployed to the desired position.

From the foregoing it can be seen that there has been provided a stent graft assembly and method which makes it possible to ensure that the graft is maintained in the desired position on the stent at all times and particularly during deployment of the stent graft while readily accommodating expansion of the stent graft after the stent graft has been deployed into the desired position. It also can be seen that use of the security rings serves to prevent inadvertent movement of the graft with respect to the stent or separation of the graft from the stent.

What is claimed:

1. A stent graft assembly for use in placing a stent graft in a vessel of a patient comprising
   a balloon delivery catheter having a distal extremity,
   a stent graft disposed over the inflatable balloon, the stent graft comprising a stent and a graft in the form of a polymeric sleeve extending over at least a portion of the stent, the graft having first and second ends and first and second expandable security rings disposed over the first and second ends of the graft and serving to secure the first and second ends of the graft to the stent to prevent inadvertent displacement of the graft with respect to the stent during deployment of the stent graft into the vessel of the patient, and
   a radiopaque marker carried by the stent or at least one of the security rings, wherein said radiopaque marker projects in a direction so that it forms a depression in the graft to help ensure that the graft and ring will not become displaced with respect to the stent.

2. An assembly as in claim 1 in which the security rings are formed of metal and have a roughened surface for engaging the outer surface of the graft to enhance frictional engagement between the security ring and the graft.

3. An assembly as in claim 1 wherein the security rings are formed of elongate metal elements having convolutions therein to permit expansion of the security ring.

4. An assembly as in claim 1 wherein one of said security rings includes an eyelet and wherein said radiopaque material is disposed in the eyelet.

5. An assembly as in claim 1 wherein said radiopaque marker projects outward from the stent.

6. An assembly as in claim 1 wherein at least one of said security rings is in the form of a stretchable polymeric material.

7. An assembly as in claim 1 wherein at least one of said security rings is in the form of a band of polymeric material having axially extending cutouts therein forming weakened regions staggered with respect to each other so that upon expansion of the security ring the weakened regions can break so that the polymeric band has a wave-like shape.

8. A method for assembling a stent graft comprising a stent and a graft onto a balloon delivery catheter comprising placing the stent graft on the delivery balloon of the delivery catheter, crimping the stent graft onto the balloon, positioning security rings on the opposite ends. of the stent graft, wherein the stent or at least one of the security rings carries a radiopaque marker that projects in a direction so that it forms a depression in the graft, and crimping the security rings onto the stent graft to ensure that the graft will not become displaced with respect to the stent during deployment of the stent graft into the vessel of the patient.

\* \* \* \* \*